(12) United States Patent
Yotani et al.

(10) Patent No.: US 9,841,406 B2
(45) Date of Patent: *Dec. 12, 2017

(54) SWITCHING VALVE FOR FLOW TYPE ANALYSIS APPARATUS

(71) Applicant: Sekisui Medical Co., Ltd., Tokyo (JP)

(72) Inventors: Takuya Yotani, Tokyo (JP); Hiroaki Taira, Tokyo (JP); Takayuki Oka, Tokyo (JP); Hideki Muraki, Tokyo (JP)

(73) Assignee: Sekisui Medical Co., Ltd. (JP)

( * ) Notice: Subject to any disclaimer, the term of this patent is extended or adjusted under 35 U.S.C. 154(b) by 137 days.

This patent is subject to a terminal disclaimer.

(21) Appl. No.: 14/786,397

(22) PCT Filed: Apr. 22, 2014

(86) PCT No.: PCT/JP2014/061256
§ 371 (c)(1),
(2) Date: Oct. 22, 2015

(87) PCT Pub. No.: WO2014/175251
PCT Pub. Date: Oct. 30, 2014

(65) Prior Publication Data
US 2016/0061788 A1 Mar. 3, 2016

(30) Foreign Application Priority Data

Apr. 22, 2013 (JP) .................. 2013-089306
Jul. 17, 2013 (JP) .................. 2013-148183

(51) Int. Cl.
*G01N 30/20* (2006.01)
*G01N 35/10* (2006.01)
*G01N 33/49* (2006.01)

(52) U.S. Cl.
CPC ........... *G01N 30/20* (2013.01); *G01N 33/491* (2013.01); *G01N 35/1097* (2013.01);
(Continued)

(58) Field of Classification Search
CPC .. G01N 30/20; G01N 33/491; G01N 35/1097; G01N 2030/201;
(Continued)

(56) References Cited

U.S. PATENT DOCUMENTS 4,476,017 A  10/1984  Scharff et al.
5,650,577 A *  7/1997  Nagai .................. F16K 3/36
                                                      436/179
(Continued)

FOREIGN PATENT DOCUMENTS

CN  101044346 A  9/2007
CN  101617226 A  12/2009
(Continued)

OTHER PUBLICATIONS

"How to Discharge Air in a Liquid Phase Pump," Instruments Information Forum/Instruments Forum, http://bbs.instrument.com.cn/topic/4637618, Apr. 3, 2013. (Machine Translation Submitted).
(Continued)

*Primary Examiner* — Hezron E Williams
*Assistant Examiner* — Marrit Eyassu
(74) *Attorney, Agent, or Firm* — Lerner, David, Littenberg, Krumholz & Mentlik, LLP

(57) ABSTRACT

A switching valve includes: (A) a rotor including: (1) a center pipe connection port, (2) a first in-valve flow path in communication with the center pipe connection port, and (3) an arc-like second in-valve flow path; (B) a stator including: (4) a first pipe connection port group which is brought into communication independently with the center pipe connection port via the first in-valve flow path when the rotor is turned, and (5) a second pipe connection port group which is brought into mutual communication via the second in-valve flow path when the rotor is turned; and (C) an arrangement of the rotor and the stator satisfying the fol-
(Continued)

lowing relationship: the state of communication or non-communication among the second pipe connection port group via the second in-valve flow path is switched in accordance with the state of communication between the first pipe connection port group and the center pipe connection port.

9 Claims, 5 Drawing Sheets

(52) U.S. Cl.
CPC . *G01N 2030/201* (2013.01); *G01N 2030/202* (2013.01); *G01N 2030/207* (2013.01)

(58) Field of Classification Search
CPC ....... G01N 2030/202; G01N 2030/207; G01N 35/1065; F01L 7/024; F16K 3/085; F16K 31/041; F16K 31/105; F16K 31/44; Y10T 137/86863; B01L 2400/0622; B01L 2400/0487; B01L 2400/0644
See application file for complete search history.

(56) References Cited

U.S. PATENT DOCUMENTS

| | | | |
|---|---|---|---|
| 5,803,117 A | 9/1998 | Olsen et al. | |
| 6,012,487 A * | 1/2000 | Hauck | F16K 11/0743 |
| | | | 137/625.11 |
| 6,382,035 B1 * | 5/2002 | Nichols | G01N 30/20 |
| | | | 73/863.72 |
| 6,453,946 B2 * | 9/2002 | Nichols | F16K 11/074 |
| | | | 137/625.15 |
| 8,322,197 B2 * | 12/2012 | Koster | G01N 30/20 |
| | | | 73/61.55 |
| 2003/0098076 A1 | 5/2003 | Nichols | |
| 2004/0035474 A1 | 2/2004 | Weiss | |
| 2010/0032604 A1 | 2/2010 | Wilen | |
| 2013/0067997 A1 | 3/2013 | Ebsen et al. | |

FOREIGN PATENT DOCUMENTS

| | | |
|---|---|---|
| CN | 102808971 A | 12/2012 |
| CN | 102918309 A | 2/2013 |
| JP | S61-20861 A | 1/1986 |
| JP | H11-153586 A | 6/1999 |
| JP | 2003-107065 A | 4/2003 |
| JP | 3832055 B2 | 10/2006 |
| JP | 2010-519535 A | 6/2010 |
| JP | 2012-026893 A | 2/2012 |
| JP | 2012-026938 A | 2/2012 |
| JP | 2012-159460 A | 8/2012 |

OTHER PUBLICATIONS

Chinese Office Action for Application No. 201480035677.7 dated Aug. 25, 2016.
Supplementary European Search Report for Application No. EP14788272 dated Dec. 1, 2016.
International Search Report from International Publication PCT/JP2014/061256 dated Aug. 5, 2014.

* cited by examiner

SWITCHING VALVE FOR FLOW TYPE ANALYSIS APPARATUS

CROSS-REFERENCE TO RELATED APPLICATIONS

The present application is a national phase entry under 35 U.S.C. §371 of International Application No. PCT/JP2014/061256 filed Apr. 22, 2014, published in Japan, which claims priority from Japanese Patent Application Nos. 2013-089306 filed Apr. 22, 2013 and 2013-148183 filed on Jul. 17, 2013, all of which are incorporated herein by reference.

TECHNICAL FIELD

The present invention relates to a switching valve for a flow type analysis apparatus. More specifically, the present invention relates to a flow type analysis apparatus provided with an air bleeding mechanism of a liquid feed pump connected via a switching valve.

BACKGROUND ART

As a conventional switching valve for flow type analysis of this type, there are a six-way two-position switching valve, a multiposition valve which selects one flow path from among a plurality of connection ports, the valve discussed in Patent Document 1, and the like. These valves are used in order to switch between an analysis column and a drain flow path that are installed on the downstream side and to switch the flow path for selecting from among a plurality of columns.

In addition, as a conventional liquid feed mechanism for flow type analysis of this type, there is a plunger reciprocating type liquid feed pump that feeds a carrier liquid (eluent) by reciprocating operations of the plunger. In a plunger reciprocating type liquid feed pump, the plunger is reciprocated inside a pump head by using a mechanism for converting the rotary motion of a drive motor into linear motion. Due to the action of a check valve and a flow path switching valve respectively provided on the side of a liquid inlet and a liquid outlet of the pump head, the carrier liquid is drawn into the pump head, and then the liquid is discharged toward a sample injection device and a detection device.

As the plunger reciprocating type liquid feed pump, there are a single plunger pump provided with a pair of plungers and a pump head and a double plunger pump including two pairs of plungers and a pump head arranged in parallel or in series. In a plunger reciprocating type liquid feed pump, the plunger is reciprocated to repeat discharge motion and suction motion to perform feeding of liquid. The motion cycle of the liquid feed pump used in a normal flow type analysis apparatus is not synchronized with the analysis time and the analysis cycle, i.e., it is independently set irrespectively of the analysis time and the analysis cycle.

In performing feeding of liquid by using the above-described pumps, it is necessary to release air from an inside of the pump as a preparation for the liquid feeding. Typically, a drain valve included in a liquid feed apparatus is opened to secure a drain flow path for releasing air before performing air bleeding by feeding a large amount of carrier liquid (e.g., the carrier liquid can be fed in the flow rate of 2 mL/min or the like). In performing this air bleeding, it is necessary that the volume corresponding to one stroke of the plunger is greater than the volume of a liquid contact portion of the check valve. The volume corresponding to one stroke of the plunger differs according to the configuration of the entire flow type analysis apparatus and can be empirically set. For example, if the volume is set in consideration of the dimension of the flow type analysis apparatus, then if the volume of the liquid contact portion of the check valve is set to be in the range of 40 to 100 µL, the volume corresponding to one stroke of the single plunger pump becomes approximately 230 µL.

REFERENCE DOCUMENT LIST

Patent Document

Patent Document 1: Japanese Patent No. 3832055

SUMMARY OF THE INVENTION

Problems to be Solved by the Invention

However, in reducing the size of a plunger of a liquid feed pump in order to achieve miniaturization of the liquid feed pump and carry out steady liquid feeding at a low flow rate, intending to reduce the size of the flow type analysis apparatus, if the volume corresponding to one stroke of the plunger is less than the volume of the liquid contact portion of the check valve of the liquid feed pump, then the air cannot be sufficiently released. As a result, a phenomenon of back current may occur due to entrained air, which may cause poor liquid feeding. More specifically, because it is required that the volume corresponding to one stroke of the plunger is greater than the volume of the liquid contact portion of the check valve sufficient to appropriately release air from the liquid feed pump, the use of a small-volume plunger pump has been difficult.

In addition, in releasing air from the plunger pump, it is necessary to open the drain valve installed in the drain flow path for air bleeding to secure the drain flow path before feeding the carrier liquid for several minutes at a high flow rate to force out the air. Accordingly, because a space is required to install the drain valve, it has been difficult to reduce the size of the flow type analysis apparatus.

In consideration of these circumstances, an object of the present invention is to provide a switching valve for flow type analysis capable of structuring a mechanism for releasing air from a plunger pump without depending on the stroke of a plunger.

In addition, another object of the present invention is to provide a switching valve for flow type analysis capable of forming a drain flow path for releasing air that does not require a drain valve.

Furthermore, another object of the present invention is to provide a small flow type analysis apparatus provided with an air bleeding mechanism that uses the switching valve and the drain flow path for releasing air that does not require installation of a drain valve.

Means for Solving the Problems

According to an aspect of the present invention for solving the above-described problem, a switching valve includes the following (A) to (C):
 (A) a rotor including the following (1) to (3):
  (1) at least one center pipe connection port;
  (2) at least one first in-valve flow path which is in communication with the center pipe connection port; and (3) at least one arc-like second in-valve flow path that turns in accordance with the turning of the first in-valve flow path and has a flow path length equal to or greater than a distance travelled by one motion of the turning;

(B) a stator including the following (4) and (5):

(4) a first pipe connection port group having at least two pipe connection ports independently and respectively in communication with the center pipe connection port via the first in-valve flow path when the first in-valve flow path of the rotor turns and of which connection positions exist on one circumference around a central axis of the rotor; and (5) a second pipe connection port group having positions of connection with the arc-like second in-valve flow path on a circumference of a circle which is coaxial in relation to and having a diameter different from the circumference on which positions of connection between the first in-valve flow path of the rotor and the first pipe connection port group exist, the second pipe connection port group having two or more pipe connection ports that are to be brought into mutual communication when the arc-like second in-valve flow path is turned; and (C) an arrangement of the rotor and the stator that satisfies the following relationships (6) and (7):

(6) at at least one of the pipe connection ports, of the first pipe connection port group of the stator that is brought into communication independently with the first in-valve flow path of the rotor, when the center pipe connection port and the pipe connection port is brought into mutual communication, two or more mutually adjacent pipe connection ports of the second pipe connection port group are brought into mutual communication via the arc-like second in-valve flow path; and (7) at the other pipe connection port of the first pipe connection port group, when the center pipe connection port and the pipe connection port are brought into mutual communication, the mutually adjacent pipe connection ports of the second pipe connection port group are not to be brought into mutual communication via the arc-like second in-valve flow path.

In order to include the above-described configuration, the switching valve according to the present invention is capable of opening and closing the flow path brought into communication via the arc-like second in-valve flow path by switching the position of connection between the center pipe connection port and the first in-valve flow path.

Note that with respect to the length of the arc-like second in-valve flow path described above in (3), the flow path brought into communication via the arc-like second in-valve flow path can be opened and closed if the length of the arc-like second in-valve flow path is equivalent to the distance travelled by the turning by one motion. Furthermore, if the length of the arc-like second in-valve flow path is equal to or shorter than an upper limit length with which the flow path brought into communication via the arc-like second in-valve flow path can be opened and closed, then the length of the arc-like second in-valve flow path may be greater than a distance travelled by one motion of the turning.

With respect to the pipe to be connected to the switching valve, the pipe may be appropriately performed in accordance with the flow path intended for the flow type analysis apparatus to be used, and the pipe is not limited to a particular type. However, if air bleeding from the liquid feed pump is intended, the present invention at least includes the following pipes provided in the following manner.

At least one of the center pipe connection ports is connected with a measuring pump.

For the first pipe connection port group brought into communication independently with the center pipe connection port via the first in-valve flow path, at least one of the pipe connection ports is connected to the cylinder chamber of the liquid feed pump.

Furthermore, the present invention includes the following pipes as the drain flow path for air bleeding.

For the second pipe connection port group that is brought into mutual communication via the second in-valve flow path when the arc-like second in-valve flow path is turned, at least one of the pipe connection ports is connected to the flow path that branches from the flow path of the liquid feed pump on the discharge side and in which the carrier liquid is allowed to flow when the air bleeding of the liquid feed pump is carried out, and another at least one of the pipe connection ports is connected to the drain flow path.

In addition, in order to carry out air bleeding from a liquid feed pump in a high pressure gradient liquid feed device including two liquid feed pumps, it is preferable to use an at least one way, at least six port, and at least four position switching valve including the following pipes and connections provided in the following manner.

At least one center pipe connection port is connected with the measuring pump.

For a first pipe connection port group having at least four pipe connection ports that are brought into communication independently with the center pipe connection port via the first in-valve flow path when the first in-valve flow path is turned, one pipe connection port is connected to the cylinder chamber of a liquid feed pump 1, one pipe connection port is connected to the cylinder chamber of a liquid feed pump 2, one pipe connection port is connected to a needle of a sample injection device, and one pipe connection port is connected to a diluting and washing liquid reservoir tank.

Note that the above-described connection is performed if the liquid feed pumps 1,2 are a single plunger pump. If the liquid feed pump includes a plurality of plungers, a pipe connection port may be connected to each cylinder chamber.

If the diluting and washing liquid reservoir tank is divided into independent reservoir tanks, one pipe connection ports may be connected to the diluent reservoir tank and the washing liquid reservoir tank, respectively, and furthermore, if a reservoir tank is provided for another reagent, one pipe connection port may be connected to each of the reservoir tanks for each reagent.

Furthermore, the present invention includes the following pipes as the drain flow path for air bleeding.

For a second pipe connection port group having at least two pipe connection ports that are brought into mutual communication when the arc-like second in-valve flow path is turned, at least one of the pipe connection ports is brought into communication with the flow path which is branched from the flow path of the liquid feed pump on the discharge side thereof and in which the carrier liquid is allowed to flow when air bleeding of the liquid feed pump is carried out, and one or more pipe connection ports are connected to the drain flow path.

In the above-described switching valve, by designing the length of the arc-like second in-valve flow path to be equal to or greater than a distance travelled by two motions of the turning, the drain flow path and the flow path that branches from the flow path of the liquid feed pump on the discharge side thereof and in which the carrier liquid is allowed to flow when the air bleeding of the liquid feed pump is carried out are brought into mutual communication via the arc-like second in-valve flow path when the measuring pump and the liquid feed pump 1 or the liquid feed pump 2 are brought into communication with each other via the first in-valve flow path.

Furthermore, when the first in-valve flow path is turned to be brought into communication with the pipe connection port with which neither the measuring pump nor the liquid feed pump is brought into communication, the drain flow path and the flow path in which the carrier liquid is allowed to flow when the air bleeding of the liquid feed pump is carried out are not brought into mutual communication when the arc-like second in-valve flow path is turned. The flow path is switched in the above-described manner, and thus, it is possible to secure the drain flow path, which is conventionally secured by the opening and closing of a drain valve, by switching between flow paths by using the switching valve.

Note that the length of the arc-like second in-valve flow path may be longer than a distance travelled by two motions of the turning if the length is within the range in which the above-described switching of the flow path can be performed.

Furthermore, if three or more pipe connection ports that are brought into communication via the arc-like second in-valve flow path are provided, a flow path connected to at least two mutually adjacent pipe connection ports can be brought into communication by appropriately setting the length of the arc-like second in-valve flow path, and the flow path can be brought into communication or closed by the turning of the first in-valve flow path.

In addition, the flow type analysis apparatus according to the present invention is constituted by the switching valve, a flow path connected via the switching valve, a sample injection device, and a separation and detection device configured to separate and detect components of a sample in a flow path for a carrier liquid provided on a downstream side of the sample injection device.

In addition, the above-described flow type analysis apparatus can be preferably used for measurement of hemoglobin components (in particular, hemoglobin A1c) for diabetes testing. Therefore, in the hemoglobin component measurement method according to the present invention, the sample injection device is used to inject blood into the flow path for the carrier liquid as the sample, hemoglobin components in the blood are separated and detected, and the amounts of the components (hemoglobin A1c values and the like) are measured.

Effects of the Invention

By using the switching valve according to the present invention to bring a measuring pump and a cylinder chamber of a liquid feed pump into mutual communication, air bleeding of an inside of the liquid feed pump can be performed by drawing and discharging a carrier liquid with the measuring pump without forcing out air from the cylinder chamber by strokes of a plunger.

As described above, air bleeding from the liquid feed pump can be performed regardless of the volume corresponding to one stroke of a plunger, and accordingly, even if a single plunger pump is used having a plunger of which the volume corresponding to one stroke is small, the phenomenon of backflow of the carrier liquid that may occur due to contamination of air through the check valve, which is the problem occurring during liquid feeding, can be suppressed, and thus, sufficient liquid feeding is made possible.

Conventionally, air bleeding of an inside of a pump is performed by feeding a carrier liquid in a large amount after a drain flow path for air bleeding is secured by opening a drain valve included in a liquid feed device. However, if the switching valve is used, in carrying out air bleeding of the liquid feed pump by bringing the measuring pump and the cylinder chamber of the liquid feed pump into mutual communication via the first in-valve flow path, the drain flow path and the flow path in which the carrier liquid is allowed to flow during the air bleeding are brought into mutual communication via the arc-like second in-valve flow path, whereas on the other hand, at positions other than the position at which the measuring pump and the cylinder chamber of the liquid feed pump are not brought into mutual communication via the first in-valve flow path, the drain flow path and the flow path in which the carrier liquid is allowed to flow during the air bleeding are not brought into mutual communication via the arc-like second in-valve flow path, and thus, the flow path is switched to the side of a column and a detection device. In other words, the switching valve enables the switching between a drain flow path for air bleeding and a flow path used during a normal operation of the liquid feed device, which is conventionally carried out by using a drain valve, and accordingly, the present invention can contribute to the reduction of the size of a flow type analysis apparatus because the present invention does not require a drain valve.

Accordingly, the present invention can contribute to the reduction of the apparatus size by configuring the flow type analysis apparatus with the switching valve.

MODE FOR CARRYING OUT THE INVENTION

Embodiments of the present invention will be described below.

First Embodiment

Figure 1:
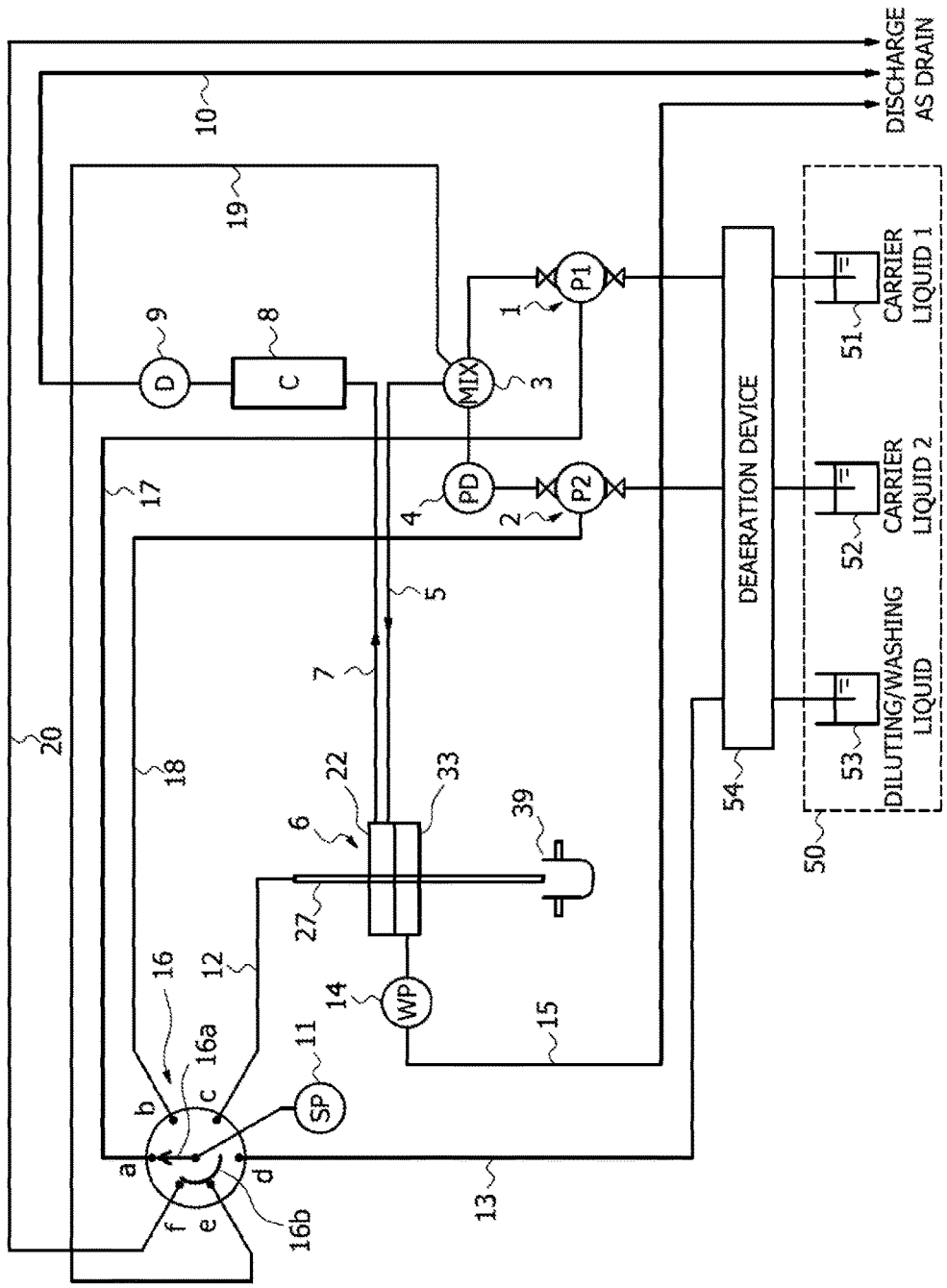
FIG. 1 is a system diagram of a flow type analysis apparatus illustrated as a first embodiment of the present invention, which includes a one-way six-port four-position switching valve.

FIG. 1 is a system diagram of a flow type analysis apparatus illustrated as a first embodiment of the present invention, which includes a one-way six-port four-position switching valve.

The flow type analysis apparatus according to the present embodiment is used to analyze components of hemoglobin, including hemoglobin A1c in blood, using the technique of high performance liquid chromatography (HPLC). Accordingly, blood is used as the sample. In addition, a hemolysis process is necessary as a pretreatment, and a blood-dissolved solution is used. However, alternatively, a diluent with which hemolysis can be performed at the same time as dilution may be used, or further alternatively, a diluting and washing liquid may be used, which serves as both the above-described diluent and as a washing liquid.

To the flow type analysis apparatus illustrated in FIG. 1, a carrier liquid reservoir tank 51,52 for storing a first carrier liquid and a second carrier liquid of different composition, including the type and the concentration of the solvent and the reagent to be added, for example, and a diluting and washing liquid reservoir tank 53 are connected via a common deaeration device 54. Note that the first and the second carrier liquid reservoir tanks 51,52 and the diluting and washing liquid reservoir tank 53 may be designed as a kit as a reagent kit 50. In addition, the diluting and washing liquid reservoir tank 53 may be divided into separate reservoir tanks, i.e., into a diluent tank 53a and a washing liquid tank 53b.

The flow type analysis apparatus illustrated in FIG. 1 is constituted by liquid feed pumps 1,2 for feeding the first and the second carrier liquid from the reservoir 51,52, a mixer 3 for mixing the carrier liquid fed from the liquid feed pump 1,2, a pulse damper 4 which is in communication with the mixer 3 and configured to absorb pulsation, a flow path 5 in which the carrier liquid from the mixer 3 flows, a sample injection device (main body) 6 to which the flow path 5 is connected at an inlet port thereof, a flow path 7 in which the carrier liquid flows and connected to the sample injection device 6 at an outlet port thereof, a column 8 and a detection unit 9 arranged in the flow path 7, and a drain flow path 10 disposed downstream thereof.

The liquid feed pumps 1,2 are each a single plunger pump and each includes a check valve (one-way valve) at a suction port and a discharge port thereof, respectively. In addition, the liquid feed pumps 1,2 are a variable volume type pump of which the discharge volume can be changed by changing the stroke of the plunger, and thus, the flow rate ratio between the two liquid feed pumps 1,2 can be changed.

The mixer 3 mixes a first carrier liquid from the liquid feed pump 1 and a second carrier liquid from the liquid feed pump 2 together. Specifically, the mixer 3 introduces two types of carrier liquids into a cylindrical container in a tangential direction to mix them together, and causes the mixed solution to be derived in the axial direction. Accordingly, by changing the flow rate ratio between the liquid feed pumps 1,2 and by mixing the carrier liquids by using the mixer 3, a carrier liquid having freely selected concentration at a level between the concentration of the first carrier liquid and that of the second carrier liquid (a gradient function) can be obtained. A pipe 19 is connected to the mixer 3, which is a pipe used for carrying out air bleeding and filling of the carrier liquid at the stage of preparation for operation of the apparatus. The pipe 19 is closed by a switching valve 16, which will be described later below, during a normal operation.

The pulse damper 4 is a diaphragm type damper which is in communication with a space within the mixer 3, and absorbs pulsations that may occur due to the use of a single plunger pump as the liquid feed pumps 1,2 particularly for reducing the size of the apparatus.

The sample injection device 6 includes a sample injection portion 22. The sample injection portion 22 is disposed between the flow path 5 for feeding the carrier liquid from the mixer 3 and the flow path 7 disposed on the downstream side thereof and is capable of injecting a sample into the carrier liquid by using the needle 27 by moving the needle 27 to a sample injection position.

In addition, the sample injection device 6 includes a sample drawing portion (vessel holding portion) 39 arranged below the sample injection portion 22. The sample drawing portion 39 can draw the sample by using the needle 27 by moving the needle 27 to a sample drawing position. Accordingly, the sample drawn by the sample drawing portion 39 is to be injected into the carrier liquid in the sample injection portion 22. Note that the drawing and the injection are carried out after connecting a measuring pump (sampling pump) 11 to a pipe 12 to the needle 27 via the switching valve 16. A hole for drawing and injecting the sample by using the needle 27 may be opened downward at the tip of the needle 27, or alternatively, it may be opened sideward on a side portion near the tip with the tip being closed.

In addition, the sample injection device 6 is provided with a washing portion 33 for washing the needle 27, which portion being formed integrally with a housing of the sample injection portion 22 and arranged at a location between the sample injection portion 22 and the sample drawing portion 39. The washing portion 33 supplies a washing liquid to the needle 27 that has been moved to a washing position to carry out washing of the needle 27. The washing is carried out after connecting the measuring pump 11 to a pipe 13 from the diluting and washing liquid reservoir tank 53 via the switching valve 16 and drawing the washing liquid and then connecting the measuring pump 11 to the pipe 12 to the needle 27 via the switching valve 16. After the washing, the washing liquid is recovered by using a drain pump (waste pump) 14 and is then discharged into a drain flow path 15.

The column 8 is disposed in the carrier liquid flow path 7 arranged downstream of the sample injection device 6, and separates the components contained in the sample from each other.

The detection unit 9, which is disposed on the downstream side of the column 8, detects the separated component and transmits a signal of the detected component to a data processing device (not illustrated). Results of the data processing by the data processing device are output as analysis results.

The flow type analysis apparatus illustrated in FIG. 1 is provided with the switching valve 16, which can be positioned at either one of four positions a to d. The four positions a to d correspond to ports a to d, respectively, and a first in-valve flow path 16a, which is in communication with the measuring pump 11, is selectively connected to one of the ports a to d when the first in-valve flow path 16a is turned. In addition, another arc-like second in-valve flow path 16b is turned in accordance with the turning of the first in-valve flow path 16a, and the ports e and f are brought into communication with each other due to this motion of the arc-like second in-valve flow path 16b at positions a and b.

The port a is connected to a cylinder chamber of the liquid feed pump 1 via a pipe 17 for bleeding of air and filling of the carrier liquid.

The port b is connected to the cylinder chamber of the liquid feed pump 2 via a pipe 18 for bleeding of air and filling of the carrier liquid.

The port c is connected to the needle 27 via the pipe 12.

The port d is connected to the diluting and washing liquid reservoir tank 53 via the pipe 13.

The port e is connected to the pipe 19 from the mixer 3 for bleeding of air and filling of the carrier liquid, and the port f is connected to a drain flow path 20.

In other words, a rotor of the switching valve 16 is provided with a center pipe connection port at which the measuring pump 11 is connected, the first in-valve flow path 16*a* which is in communication with the center pipe connection port, and the arc-like second in-valve flow path 16*b* which turns in accordance with the turning of the first in-valve flow path 16*a*.

A stator of the switching valve 16 is provided with a first pipe connection port group including the above-described ports a to d, and a second pipe connection port group including the above-described ports e and f.

The first pipe connection port group (the ports a to d) is in communication with the center pipe connection port via the first in-valve flow path 16*a* individually in accordance with the turning of the first in-valve flow path 16*a*, and the positions of connection between the first in-valve flow path 16*a* and each of the ports a to d exist on the same circumference.

The second pipe connection port group (the ports e and f) can be brought into communication with each other via the arc-like second in-valve flow path 16*b* in accordance with the turning of the arc-like second in-valve flow path 16*b*. The positions of connection between the arc-like second in-valve flow path 16*b* and each of the ports e and f exist on the circumference that is coaxial with the circumference on which the ports a to d exist, of which the diameter is different from that of the circumference on which the ports a to d exist.

At the ports a and b among the first pipe connection port group, the two ports e and f of the second pipe connection port group are brought into communication by the arc-like second in-valve flow path 16*b* when the center pipe connection port is brought into communication with the port a or b.

At the other ports c and d among the first pipe connection port group, the two ports e and f of the second pipe connection port group are not brought into mutual communication by the arc-like second in-valve flow path 16*b* when the center pipe connection port is brought into communication with the port c or d.

The air bleeding and the filling of the carrier liquid will be described below, which is carried out at the stage of preparation of operation of the flow type analysis apparatus illustrated in FIG. 1.

At the stage of preparation for the operation, the following operations are carried out in an automatic operation mode to fill the inside of the flow path with the liquid by releasing air from the inside of the flow path.

Figure 2:
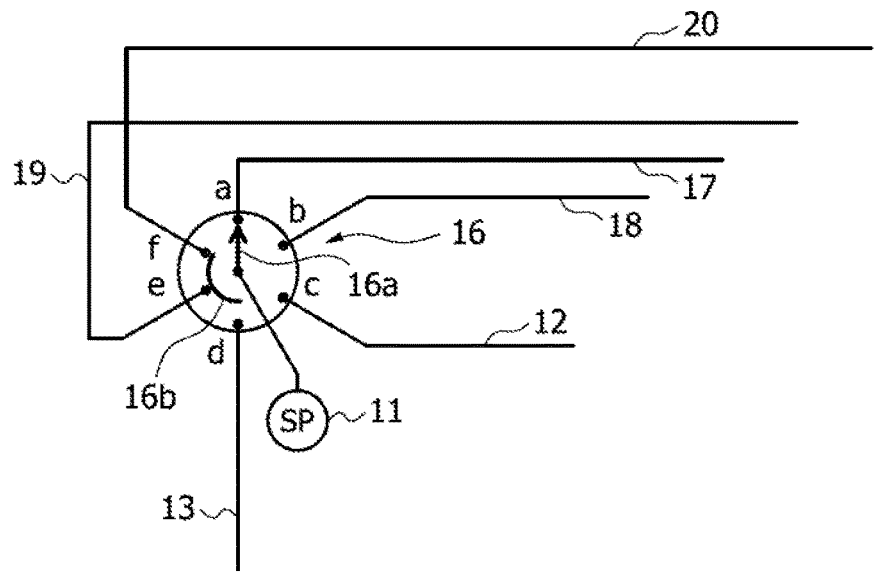
FIG. 2 is a diagram illustrating a flow path in a valve when the measuring pump is brought into communication with a port a in the system diagram of FIG. 1.

The position of the switching valve 16 is switched to the position a (the state illustrated in FIGS. 1 and 2). At the position a, the measuring pump 11 is connected to the port a (the pipe 17) and the port e and the port f are brought into communication with each other.

In this state, first, the measuring pump 11 carries out the drawing operation. Then, the first carrier liquid in the reservoir tank 51 is fed through the check valve on the drawing side of the liquid feed pump 1, then through the pipe 17 from the cylinder chamber of the liquid feed pump 1 to be drawn into the measuring pump 11. In this manner, the flow paths from the reservoir tank 51 to the liquid feed pump 1 are filled with the carrier liquid.

Next, the measuring pump 11 carries out the discharge operation. Then the first carrier liquid is pumped from the measuring pump 11 into the liquid feed pump 1 via the pipe 17, and the check valve on the discharge side is opened to allow the carrier liquid flow to be fed into the mixer 3. Furthermore, the carrier liquid is then allowed to flow into the pipe 19 from the mixer 3 due to the resistance force from the column 8, and it is further discharged from the pipe 19 as a drain through the drain flow path 20 connected to the pipe 19 via the switching valve 16 (the ports e and f).

Figure 3:
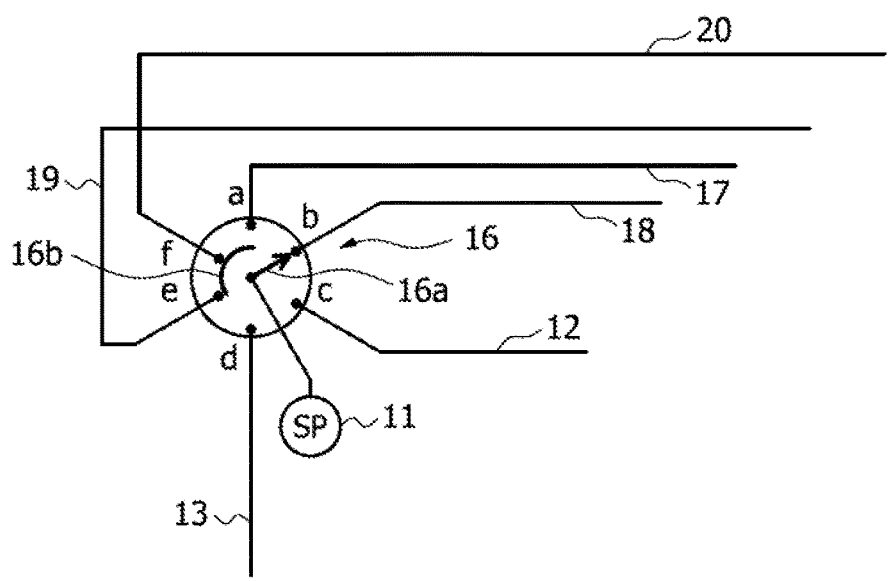
FIG. 3 is a diagram illustrating a flow path in a valve when the measuring pump is brought into communication with a port b in the system diagram of FIG. 1.

Next, the switching valve 16 is allowed to turn clockwise by 60° to position the switching valve 16 at the position b (a state illustrated in FIG. 3). At the position b, the measuring pump 11 is brought into communication with the port b (the pipe 18) and the ports e and f continue their mutual communication.

In this state, first, the measuring pump 11 carries out the drawing operation. Then, the second carrier liquid in the reservoir tank 52 is fed through the check valve on the drawing side of the liquid feed pump 2, then is fed from the cylinder chamber of the liquid feed pump 2, to be drawn into the measuring pump 11 through the pipe 18. In the above-described manner, the flow paths from the second carrier liquid reservoir tank 52 to the liquid feed pump 2 are filled with the carrier liquid.

Next, the measuring pump 11 carries out the discharge operation. Then the second carrier liquid in the measuring pump 11 is pumped into the liquid feed pump 2 via the pipe 18, then the check valve on the discharge side is opened to allow the carrier liquid to flow into the mixer 3. Furthermore, the carrier liquid is then allowed to flow into the pipe 19 from the mixer 3 due to the resistance force from the column 8, and is further discharged from the pipe 19 as a drain through the drain flow path 20 connected to the pipe 19 via the switching valve 16 (the ports e and f).

Next, the switching valve 16 is moved to a position other than the positions a and b to start the feeding from the liquid feed pumps 1,2 and fill the carrier liquid flow paths 5 and 7 including the sample injection portion 22 and the column 8 and the detection unit 9 with the carrier liquid.

A dilution step, a sample drawing step, a sample injection step, and a washing step carried out during a normal operation state of the flow type analysis apparatus illustrated in FIG. 1 will be described below.

In the dilution step, the needle 27 is positioned at a sample drawing position (the sample drawing portion 39), i.e., at a position in an inside of a vessel containing the sample.

Figure 5:
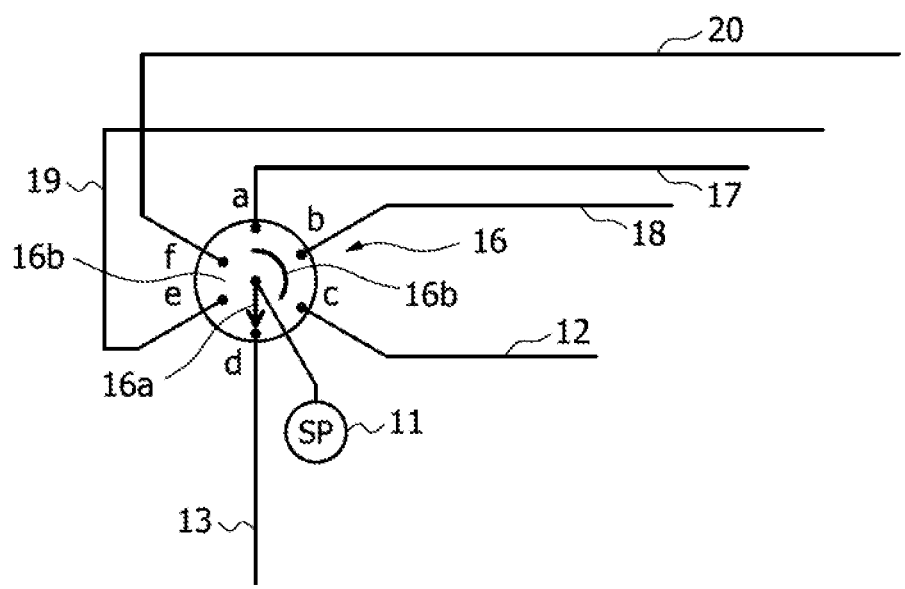
FIG. 5 is a diagram illustrating a flow path in a valve when the measuring pump is brought into communication with a port d in the system diagram of FIG. 1.

For the position of the switching valve 16, the switching valve 16 is positioned at the position d first (a state illustrated in FIG. 5). At the position d, the measuring pump 11 is connected to the port d (the pipe 13). In this state, the measuring pump 11 carries out the drawing operation. Then the diluent (the diluting and washing liquid) in the reservoir tank 53 is drawn into the measuring pump 11 via the pipe 13.

Figure 4:
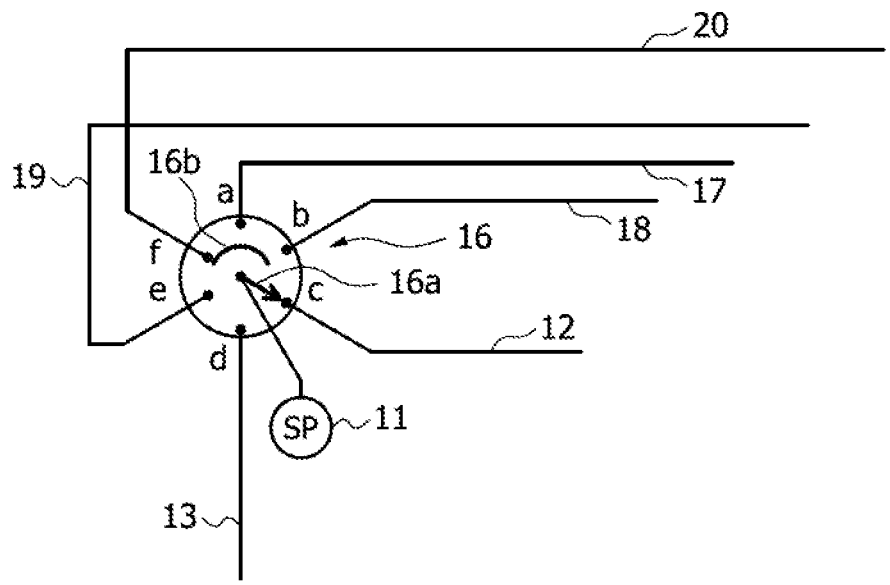
FIG. 4 is a diagram illustrating a flow path in a valve when the measuring pump is brought into communication with a port c in the system diagram of FIG. 1.

Next, the position of the switching valve 16 is changed to the position c (a state illustrated in FIG. 4). At the position c, the measuring pump 11 is connected to the port c (the pipe 12). In this state, the measuring pump 11 carries out the discharge operation. Then, the diluent in the measuring pump 11 is pumped into the needle 27 via the pipe 12. The needle 27 is positioned at the sample drawing position (the sample drawing portion 39), i.e., at a position inside the container, and thus, the diluent is supplied into the vessel. The measuring pump 11 repeats the drawing operation and the discharge operation, and thus, the needle 27 draws and returns the mixed solution including the sample and the diluent in the vessel, and thereby, the mixed solution in the vessel is stirred and the sample is homogeneously diluted.

In the sample drawing step, the needle 27 is positioned at the sample drawing position (the sample drawing portion 39), i.e., at a position inside the vessel containing the sample (the sample diluted with the diluent).

The position of the switching valve 16 is set to the position c (FIG. 4). At the position c, the measuring pump 11 is connected to the port c (the pipe 12). In this state, the measuring pump 11 carries out the drawing operation. Then, the sample in the vessel is drawn into the needle 27.

In the sample injection step, the needle 27 is positioned at the sample injection position (the sample injection portion 22).

The position of the switching valve 16 is set to the position c (FIG. 4). At the position c, the measuring pump 11 is connected to the port c (the pipe 12). In this state, the measuring pump 11 carries out the discharge operation. Then, the sample in the needle 27 is injected into the sample injection portion 22 arranged between the carrier liquid flow paths 5 and 7.

In the washing step, the needle 27 is positioned at the washing position (the washing portion 33).

The position of the switching valve 16 is set to the position d (FIG. 5) first. At the position d, the measuring pump 11 is connected to the port d (the pipe 13). In this state, the measuring pump 11 carries out the drawing operation. Then, the washing liquid (the diluting and washing liquid) in the reservoir tank 53 is drawn into the measuring pump 11 via the pipe 13.

Next, the position of the switching valve 16 is set to the position c (FIG. 4). At the position c, the measuring pump 11 is connected to the port c (the pipe 12). In this state, the measuring pump 11 carries out the discharge operation. Then, the washing liquid in the measuring pump 11 is pumped into the needle 27 via the pipe 12. The needle 27 is positioned at the washing position, and the needle 27 is washed with the washing liquid there. After the washing, the washing liquid is recovered by the drain pump 14 and is then discharged through the drain flow path 15 as a drain. In this step, because the flow rate of the drain pump 14 is higher than the flow rate of the measuring pump 11, the washing liquid after the washing is discharged from the drain flow path 15 together with the air that entered through a guide hole (not illustrated) of the needle 27 without any leakage to the outside. The washing liquid is mixed with air to take the form of a mist, and thereby, the efficiency of the washing can be increased, the consumption of the washing liquid can be reduced, and accordingly, the washing of the needle 27 can be suitably carried out.

Next, a series of operations of the switching valve 16 will be described below by referring to an example of a case in which values of hemoglobin A1c in blood are measured for diabetes testing.

First, a preparation step (the air bleeding and carrier liquid filling step) is carried out. In this step, as described above, the measuring pump 11 carries out the drawing and discharge operations with the switching valve 16 being positioned at the position a, then the switching valve 16 is positioned at the position b to carry out other drawing and discharge operations, and then, the switching valve 16 is moved to a position other than the position a or b to start the feeding from the liquid feed pumps 1,2, and thereby, the flow paths 5,7 including the sample injection portion 22 and the column 8 and the detection unit 9 are filled with the carrier liquid.

Next, a preliminary washing step (S1) is carried out. At this time, the needle 27 has been moved to the washing position.

S1-1: The position of the switching valve 16 is switched to the position d for connecting the measuring pump 11 with the diluting and washing liquid reservoir tank 53 and the measuring pump 11 measures and draws the diluting and washing liquid (washing liquid).

S1-2: After the drawing, the position of the switching valve 16 is switched to the position c for connecting the measuring pump 11 with the needle 27.

S1-3: The drain pump 14 is turned ON.

S1-4: The measuring pump 11 carries out the discharge operation to feed the washing liquid to the needle 27 and discharge the washing liquid from the washing portion 33 so that the needle 27 and the washing portion 33 are washed.

S1-5: The drain pump 14 is turned OFF. At this timing, the washing portion 33 is filled with the remaining liquid.

Next, a dilution step (S2) is carried out.

S2-1: The position of the switching valve 16 is switched to the position d for connecting the measuring pump 11 with the diluting and washing liquid reservoir tank 53, and the measuring pump 11 measures and draws the diluting and washing liquid (diluent).

S2-2: After the drawing, the position of the switching valve 16 is switched to the position c for connecting the measuring pump 11 with the needle 27.

S2-3: The needle 27 is moved by a needle moving device to a lowermost position so that the needle 27 is positioned at a position at which it faces the inside of the vessel (i.e., at the same position as the sample drawing position).

S2-4: The measuring pump 11 carries out the discharge operation to feed the diluent to the needle 27 so that the diluent is fed into the vessel via the needle 27.

S2-5: A separately measured sample (tested blood) is added into the vessel manually or automatically. Note that the filling of the separately measured sample (testing blood) is not limited to the filling after S2-4, and filling of the separately measured sample (testing blood) may be alternatively carried out previously to S2-4.

S2-6: The needle 27 is lifted from the level of the liquid in the vessel by using the needle moving device (not illustrated) so that the needle 27 is positioned at a position at which the needle 27 can draw air. Then, the measuring pump 11 carries out the suction operation to draw air for separation. The air for separation is used to prevent diffusion of the diluent remaining in the needle 27 and the diluted sample drawn for subsequent stirring in the border portion.

S2-7: The needle 27 is moved by the needle moving device again to the lowermost position.

S2-8: The measuring pump 11 repeats the drawing and discharge operations to allow the needle 27 to draw and return the mixed solution of the sample and the diluent in the vessel, and thus, the mixed solution in the vessel is stirred and the sample is homogeneously diluted and hemolyzed. Finally, the measuring pump 11 carries out the discharge operation to discharge the air for separation. The air for separation is discharged to prevent the air for separation from entering the analysis line in the subsequent sample injection step and producing noise.

Next, the sample drawing and injection step (S3) is carried out.

S3-1: The measuring pump 11 carries out measurement and drawing at the sample drawing position so that the diluted and hemolyzed sample in the vessel is drawn into the needle 27.

S3-2: The needle 27 is lifted by the needle moving device to move the needle 27 to the sample injection position at which the needle 27 faces the carrier liquid flow path (the sample injection portion 22). Then, the measuring pump 11 carries out the discharge operation to inject a predetermined amount of sample into the flow of the carrier liquid.

S3-3: The needle 27 is moved by the needle moving device to the washing position. The contamination by the sample that has adhered to an outer surface of the needle 27 is washed away by using the washing liquid that fills the inside of the washing portion 33.

S3-4: The injected sample is separated in the column 8 arranged on the downstream side so that the separated component is detected by the detection unit 9.

Next, the post-washing step (S4) is carried out.

S4-1: The drain pump 14 is turned ON.

S4-2: The measuring pump 11 carries out the discharge operation at the washing position to dispose of the sample remaining in the needle 27.

S4-3: The switching valve 16 is switched to the side of the diluting and washing liquid reservoir tank 53 (the position d) to carry out measurement and drawing of the diluting and washing liquid (washing liquid) by using the measuring pump 11. After the drawing, the switching valve 16 is switched to the side of the needle 27 (the position c).

S4-4: The measuring pump 11 carries out the discharge operation to feed the washing liquid into the needle 27 and wash the needle 27 and the washing portion 33.

S4-5: The drain pump 14 is turned OFF.

To analyze a next sample, steps S2 to S4 are repeated.

Second Embodiment

Figure 6:
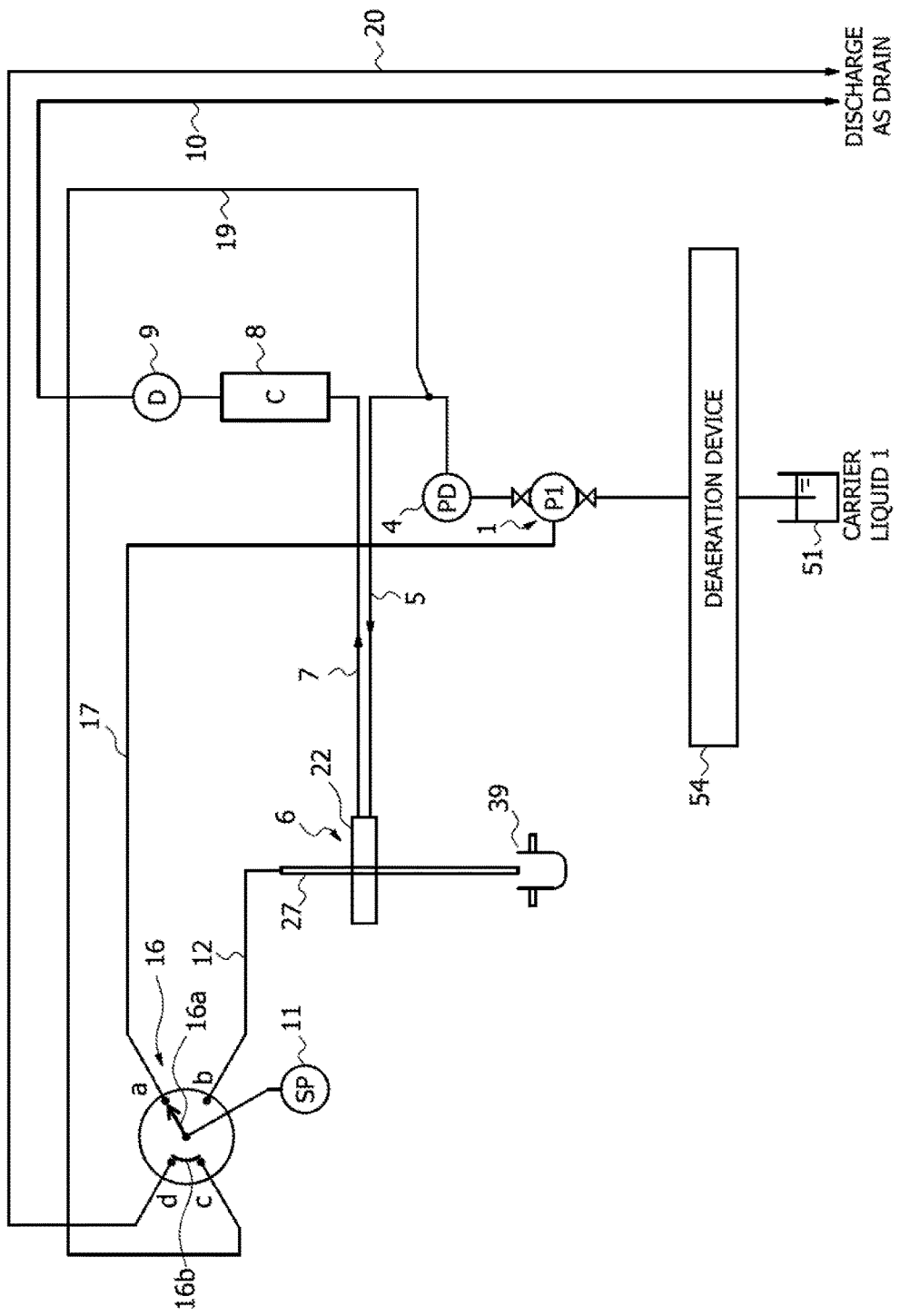
FIG. 6 is a system diagram of a flow type analysis apparatus illustrated as a second embodiment of the present invention, which includes a one-way four-port two-position switching valve.

FIG. 6 is a system diagram of a flow type analysis apparatus illustrated as a second embodiment of the present invention, which includes a one-way four-port two-position switching valve.

The flow type analysis apparatus according to the present embodiment is used to carry out isocratic analysis for performing analysis using the technique of HPLC and without changing the composition of the carrier liquid.

The first carrier liquid reservoir tank 51 is connected to a flow type analysis apparatus via the deaeration device 54 illustrated in FIG. 6.

The flow type analysis apparatus illustrated in FIG. 6 includes a liquid feed pump 1 for feeding the first carrier liquid from the reservoir tank 51, the pulse damper 4 configured to absorb pulsation, the carrier liquid flow path 5, the sample injection device (main body) 6 to which the flow path 5 is connected at an inlet port thereof, a carrier liquid flow path 7 connected to the sample injection device 6 at an outlet port thereof, the column 8 and a detection unit 9 arranged in the flow path 7, and a drain flow path 10 disposed downstream thereof.

The first carrier liquid feed pump 1 is a single plunger pump which includes a check valve (one-way valve) at a drawing port and a discharge port thereof, respectively. The liquid feed pump 1 may be a variable volume type pump of which the discharge volume can be changed by changing the stroke of the plunger. The pipe 19 is connected to the flow path 5 for feeding the carrier liquid from 1, which is a pipe used in the air bleeding and filling of the liquid at the stage of preparation for operation of the apparatus. In a normal operation state of the apparatus (i.e., during the sample drawing step and the sample injection step), the pipe 19 is closed by the switching valve 16, which will be described below.

The pulse damper 4 is a diaphragm type damper which absorbs pulsations that may occur due to the use of a single plunger pump as the liquid feed pump 1.

The sample injection device 6 includes a sample injection portion 22. The sample injection portion 22 is disposed between the flow path 5 for feeding the carrier liquid from the liquid feed pump 1 and the flow path 7 disposed on the downstream side thereof, and capable of injecting a sample into the carrier liquid by using the needle 27 by moving the needle 27 to a sample injection position.

In addition, the sample injection device 6 includes a sample drawing portion (vessel holding portion) 39 arranged below the sample injection portion 22. The sample drawing portion 39 can draw the sample by using the needle 27 by moving the needle 27 to a sample drawing position. Accordingly, the sample drawn by the sample drawing portion 39 is to be injected into the carrier liquid in the sample injection portion 22. Note that the drawing and the injection are carried out after connecting a measuring pump 11 to a pipe 12 to the needle 27 via the switching valve 16.

The column 8 is disposed in the carrier liquid flow path 7 arranged downstream of the sample injection device 6, and separates the components contained in the sample from one another.

The detection unit 9, which is disposed on the downstream side of the column 8, detects the separated component and transmits a signal of the detected component to a data processing device (not illustrated). Results of the data processing by the data processing device are output as analysis results.

The flow type analysis apparatus illustrated in FIG. 6 is provided with the switching valve 16, which can be positioned at either of two positions a and b. The two positions a and b correspond to ports a and b, respectively, and a first in-valve flow path 16a, which is in communication with the measuring pump 11, is selectively connected to one of the ports a and b when the first in-valve flow path 16a is turned. In addition, another arc-like second in-valve flow path 16b is turned in accordance with the turning of the first in-valve flow path 16a, and the ports c and d are brought into communication with each other due to this motion of the arc-like second in-valve flow path 16b at the position a.

The port a is connected to a cylinder chamber of the liquid feed pump 1 via a pipe 17 for bleeding of air and filling of the carrier liquid.

The port b is connected to the needle 27 via the pipe 12.

The port c is connected to the pipe 19 for releasing of air and filling of the carrier liquid connected from the pulse damper 4.

The port d is connected to the drain flow path 20.

In the present embodiment, the ports a and b are equivalent to the first pipe connection port group and the ports c and d are equivalent to the second pipe connection port group.

The air bleeding and the filling of the carrier liquid will be described below, which is carried out at the stage of preparation of operation of the flow type analysis apparatus illustrated in FIG. 6.

At the stage of preparation for operation, the following operations are carried out in an automatic operation mode to fill the inside of the flow path with the liquid by releasing air from the inside of the flow path.

Figure 7:
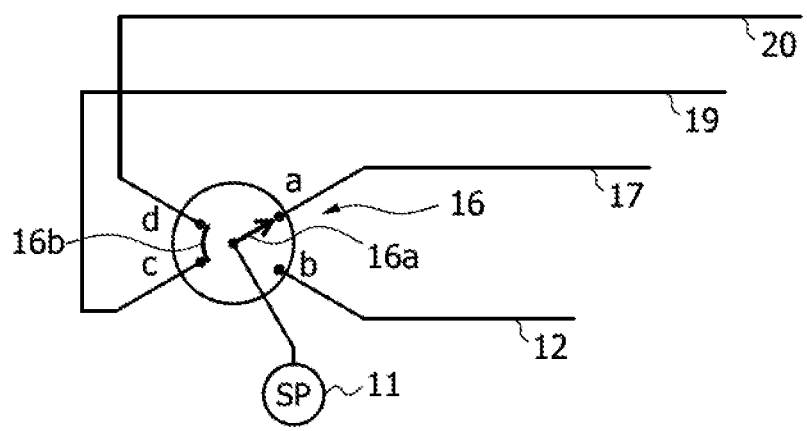
FIG. 7 is a diagram illustrating a flow path in a valve when the measuring pump is brought into communication with a port a in the system diagram of FIG. 1.

The position of the switching valve 16 is switched to the position a (the state illustrated in FIGS. 6 and 7). At the position a, the measuring pump 11 is connected to the port a (the pipe 17) and the port c and the port d are brought into communication with each other.

In this state, first, the measuring pump 11 carries out the drawing operation. Then, the first carrier liquid in the reservoir tank 51 flows through the check valve on the drawing side of the liquid feed pump 1, then through the pipe 17 from the cylinder chamber of the liquid feed pump 1 to be drawn into the measuring pump 11. In this manner, the flow paths from the reservoir tank 51 to the liquid feed pump 1 are filled with the carrier liquid.

Next, the measuring pump 11 carries out the discharge operation. Then, the first carrier liquid is pumped from the measuring pump 11 into the liquid feed pump 1 via the pipe 17, and the check valve on the discharge side is opened to let the carrier liquid flow into the pulse damper 4. Furthermore, the carrier liquid is then allowed to flow into the pipe 19 from the pulse damper 4 due to the resistance force from the column 8, and because the pipe 19 is in communication with the drain flow path 20 via the switching valve 16 (the ports c and d), the carrier liquid is discharged from the drain flow path 20 as a drain.

The sample drawing step and the sample injection step carried out in the normal operation state of the flow type analysis apparatus illustrated in FIG. 6 will be described below.

In the sample drawing step, the needle 27 is positioned at the sample drawing position (the sample drawing portion 39), i.e., at a position inside the vessel containing the sample.

Figure 8:
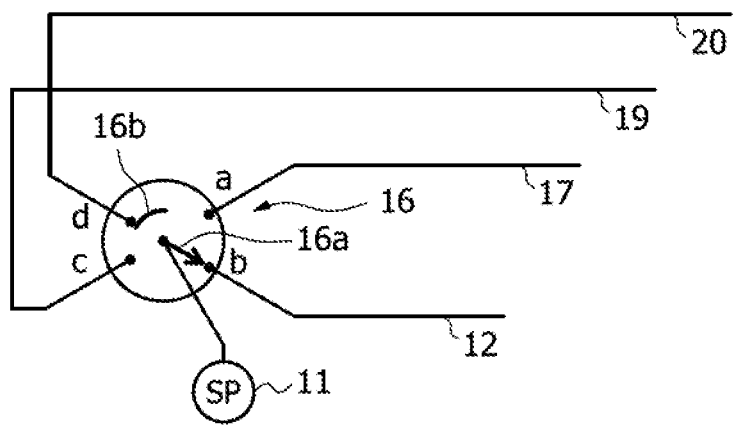
FIG. 8 is a diagram illustrating a flow path in a valve when the measuring pump is brought into communication with a port b in the system diagram of FIG. 1.

The position of the switching valve 16 is set to the position b (FIG. 8). At the position b, the measuring pump 11 is connected to the port b (the pipe 12). In this state, the measuring pump 11 carries out the drawing operation. Then, the sample in the vessel is drawn into the needle 27.

In the sample injection step, the needle 27 is positioned at the sample injection position (the sample injection portion 22).

The position of the switching valve 16 is switched to the position b (FIG. 8). At the position b, the measuring pump 11 is connected to the port b (the pipe 12). In this state, the measuring pump 11 carries out the discharge operation. Then, the sample in the needle 27 is injected into the sample injection portion 22 arranged between the carrier liquid flow paths 5 and 7.

According to the first embodiment, an apparatus for feeding the diluting and washing liquid is constituted by the measuring pump 11, and the measuring pump 11 can be connected selectively to an upper end portion of the needle 27 or the diluting and washing liquid reservoir tank 53, and the diluting and washing liquid having been drawn from the reservoir tank 53 when the switching valve 16 is positioned at one position (the position d) can be discharged and fed into the needle 27 when the switching valve 16 is positioned at another position (the position c), and thereby, the feeding of the diluting and washing liquid can be easily carried out, which makes the present invention highly useful.

According to the first embodiment and the second embodiment, air bleeding can be suitably performed even with a small-size and low-volume plunger pump, with which air bleeding by the stroke of the plunger is difficult to perform, by using an air bleeding mechanism constituted by the connection between the measuring pump 11 and the cylinder chamber of the liquid feed pumps 1,2 (the cylinder chamber of the liquid feed pump 1 in the second embodiment) by using the switching valve 16, and thus, the plunger pump can be used as the configuration of the flow type analysis apparatus, and therefore, the present invention can contribute to reduction of the size of the flow type analysis apparatus.

According to the first embodiment and the second embodiment, the flow path can be switched between the flow path for air bleeding and the flow path for normal operation due to the effect of switching of the flow path with the arc-like second in-valve flow path 16b included in the switching valve 16, and thus no drain valve is required, and therefore the present invention can contribute to reduction in the size of the flow type analysis apparatus.

In addition, the hemoglobin component measurement method according to the embodiments of the present invention can contribute to increasing the accuracy and the speed of diabetes testing, in which method, blood is injected into the carrier liquid flow path as the sample, the hemoglobin components in the blood are separated and detected, and the amounts of the components thereof (hemoglobin A1c values, and the like) are measured. As a method for separating and detecting hemoglobin components in blood and measuring the component amount thereof, a known method can be used. As such a known method, separation analysis performed according to standard liquid chromatography including a sample injection portion, a sample separation portion having a separation column, a detection portion, and the like, is well known to a person skilled in the art. However, the scope of application of the apparatus of the present invention is not limited to this.

Note that the embodiments described above with reference to the drawings are mere examples of the present invention, and the present invention can of course include not only the invention directly illustrated by the embodiments described above, but also various alterations and modifications by one skilled in the art within the scope of the present invention as claimed in the claims.

INDUSTRIAL APPLICABILITY

The switching valve for flow type analysis according to the present invention, the flow type analysis apparatus which uses the switching valve, and the hemoglobin component measurement method can be suitably used for various types of analysis, and therefore, the industrial applicability is high.

REFERENCE SYMBOL LIST

1 First liquid feed pump (single plunger pump)
2 Second liquid feed pump (single plunger pump)
3 Mixer
4 Pulse damper
5 Carrier liquid flow path
6 Sample injection device (main body)
7 Carrier liquid flow path
8 Column
9 Detection unit
10 Drain flow path
11 Measuring pump (Sampling pump)
12 Pipe
13 Pipe
14 Drain pump (Waste pump)
15 Drain flow path
16 Switching valve
16a First in-valve flow path
16b Second in-valve flow path
17 Pipe
18 Pipe
19 Pipe 20 Drain flow path
22 Sample injection portion
27 Needle
33 Washing portion
39 Sample suction portion (vessel holding portion)
50 Reagent kit
51 First carrier liquid reservoir tank
52 Second carrier liquid reservoir tank
53 Diluting and washing liquid reservoir tank
54 Deaeration device

The invention claimed is:

1. A switching valve for a flow type analysis apparatus comprising:
   (A) a rotor comprising:
      (1) at least one center pipe connection port;
      (2) at least one first in-valve flow path in communication with the center pipe connection port; and
      (3) at least one arc-like second in-valve flow path turning in accordance with turning of the first in-valve flow path and have a flow path length equal to or greater than a distance travelled by one motion of the turning;
   (B) a stator comprising:
      (4) a first pipe connection port group having at least two pipe connection ports independently and respectively in communication with the center pipe connection port via the first in-valve flow path when the first in-valve flow path of the rotor turns and of which connection positions exist on one circumference around a central axis of the rotor; and
      (5) a second pipe connection port group having positions of connection with the arc-like second in-valve flow path on a circumference of a circle coaxial in relation to and having a diameter different from the circumference on which positions of connection between the first in-valve flow path of the rotor and the first pipe connection port group exist, the second pipe connection port group having two or more pipe connection ports that are to be brought into mutual communication when the arc-like second in-valve flow path is turned; and
   (C) an arrangement of the rotor and the stator that satisfies the following relationships (6) and (7):
      (6) at at least one of the pipe connection ports, of the first pipe connection port group of the stator that is brought into communication independently with the first in-valve flow path of the rotor, when the center pipe connection port and the pipe connection port are brought into mutual communication, at least two mutually adjacent pipe connection ports of the second pipe connection port group are brought into mutual communication via the arc-like second in-valve flow path; and
      (7) at the other pipe connection port of the first pipe connection port group, when the center pipe connection port and the pipe connection port are brought into mutual communication, the mutually adjacent pipe connection ports of the second pipe connection port group are not to be brought into mutual communication via the arc-like second in-valve flow path.

2. The switching valve according to claim 1, wherein the arc-like second in-valve flow path of the rotor has a flow path length greater than a distance travelled by one motion of the turning.

3. The switching valve according to claim 1, wherein the switching valve is an at least one way, at least six port, and at least four position switching valve, wherein the arc-like second in-valve flow path of the rotor has a flow path length equal to or greater than a distance travelled by two motions of the turning,
wherein the first pipe connection port group of the stator includes four or more pipe connection ports that are independently brought into communication with the center pipe connection port via the first pipe connection port group of the rotor, and
wherein the second pipe connection port group of the stator includes two or more pipe connection ports that are in mutual communication via the arc-like second in-valve flow path of the rotor.

4. The switching valve according to claim 3, wherein the arc-like second in-valve flow path of the rotor has a flow path length greater than a distance travelled by two motions of the turning.

5. A flow type analysis apparatus including a liquid feed pump, comprising:
   a switching valve comprising:
      (A) a rotor comprising:
         (1) at least one center pipe connection port;
         (2) at least one first in-valve flow path in communication with the center pipe connection port; and
         (3) at least one arc-like second in-valve flow path turning in accordance with turning of the first in-valve flow path and have a flow path length equal to or greater than a distance travelled by one motion of the turning;
      (B) a stator comprising:
         (4) a first pipe connection port group having at least two pipe connection ports independently and respectively in communication with the center pipe connection port via the first in-valve flow path when the first in-valve flow path of the rotor turns and of which connection positions exist on one circumference around a central axis of the rotor; and
         (5) a second pipe connection port group having positions of connection with the arc-like second in-valve flow path on a circumference of a circle coaxial in relation to and having a diameter different from the circumference on which positions of connection between the first in-valve flow path of the rotor and the first pipe connection port group exist, the second pipe connection port group having two or more pipe connection ports that are to be brought into mutual communication when the arc-like second in-valve flow path is turned; and
      (C) an arrangement of the rotor and the stator that satisfies the following relationships (6) and (7):
         (6) at at least one of the pipe connection ports, of the first pipe connection port group of the stator that is brought into communication independently with the first in-valve flow path of the rotor, when the center pipe connection port and the pipe connection port are brought into mutual communication, at least two mutually adjacent pipe connection ports of the second pipe connection port group are brought into mutual communication via the arc-like second in-valve flow path; and
         (7) at the other pipe connection port of the first pipe connection port group, when the center pipe connection port and the pipe connection port are brought into mutual communication, the mutually adjacent pipe connection ports of the second pipe connection port group are not to be brought into mutual communication via the arc-like second in-valve flow path, wherein the center pipe connection port of the switching valve is connected to a measuring pump via a pipe, and wherein at least one of the first pipe connection port group of the switching valve is connected to a cylinder chamber of the liquid feed pump via a pipe.

6. The flow type analysis apparatus according to claim 5, wherein a flow path which is branched from a flow path of the liquid feed pump on a discharge side thereof and in which a carrier liquid is allowed to flow when air bleeding of the liquid feed pump is carried out is connected to at least one of the pipe connection ports of the second pipe connection port group of the switching valve, and wherein a drain flow path is connected to the other pipe connection port of the second pipe connection port group.

7. An air bleeding method, wherein the air bleeding of the liquid feed pump is carried out by using the flow type analysis apparatus according to claim 5 and by feeding the carrier liquid by performing suction and discharge operations by using the measuring pump.

8. A flow path switching method carried out by the flow type analysis apparatus according to claim 6, wherein when the measuring pump and the cylinder chamber of the liquid feed pump are brought into mutual communication via the first in-valve flow path, the drain flow path and the flow path which is branched from a flow path of the liquid feed pump on the discharge side thereof and in which the carrier liquid is allowed to flow when the air bleeding of the liquid feed pump is carried out are brought into mutual communication via the arc-like second in-valve flow path, and furthermore, wherein when the first in-valve flow path is turned to be brought into communication with a pipe connection port to which neither the measuring pump nor the cylinder chamber of the liquid feed pump is brought into communication, the drain flow path and the flow path in which the carrier liquid is allowed to flow when the air bleeding of the liquid feed pump is carried out are not to be brought into mutual communication when the arc-like second in-valve flow path is turned.

9. A hemoglobin component measurement method, wherein the flow type analysis apparatus according to claim 5 is used to separate and detect hemoglobin components in blood and to measure the amounts of the components detected.

* * * * *